US007753865B1

(12) United States Patent
Hely

(10) Patent No.: US 7,753,865 B1
(45) Date of Patent: Jul. 13, 2010

(54) HIGHLY STABLE ANKLE BRACE

(75) Inventor: John P. Hely, Roanake, TX (US)

(73) Assignee: Weber Orthopedic Inc., Santa Paula, CA (US)

( * ) Notice: Subject to any disclaimer, the term of this patent is extended or adjusted under 35 U.S.C. 154(b) by 661 days.

(21) Appl. No.: 11/653,131

(22) Filed: Jan. 16, 2007

(51) Int. Cl.
*A61F 5/00* (2006.01)
(52) U.S. Cl. .............................. 602/23; 602/27; 128/882
(58) Field of Classification Search ................ 602/5, 602/20–21, 23, 26–29, 60–62; 128/882
See application file for complete search history.

(56) References Cited

U.S. PATENT DOCUMENTS

| 5,067,486 | A | | 11/1991 | Hely | |
|---|---|---|---|---|---|
| 5,899,872 | A | * | 5/1999 | Gilmour | .................. 602/65 |
| 6,117,098 | A | | 9/2000 | Weber | |
| 6,929,617 | B2 | * | 8/2005 | McCormick et al. | .......... 602/65 |
| 2004/0260226 | A1 | * | 12/2004 | Gilmour | .................. 602/65 |

\* cited by examiner

*Primary Examiner*—Michael A. Brown
(74) *Attorney, Agent, or Firm*—William W. Haefliger

(57) ABSTRACT

In ankle brace apparatus, the combination comprising a foot and ankle holder having a lower foot portion, and having an upper ankle portion with opposite first and second sides, said upper ankle portion including: a guide loop having opposite sections, a first orthopedic strap anchored to one section for passing about a user's ankle or lower leg, and then passage through the loop to extend in a first tightening direction, a second orthopedic strap anchored to another said section to extend in a second and opposite tightening direction, relative to said ankle or lower leg, whereby the two straps extending in said first and second directions can be manually pulled in said directions to tighten the first strap about said ankle or lower leg, and the two tensioned straps then connected by push together connection to tightened extents of the first strap to hold tension transmission via said loop sections and straps; and support strap structure operatively connected to said holder to extend under said foot portion and then to extend generally upwardly and rearwardly for removable retention to at least one of said opposite sides at a retention zone, or zones.

18 Claims, 6 Drawing Sheets

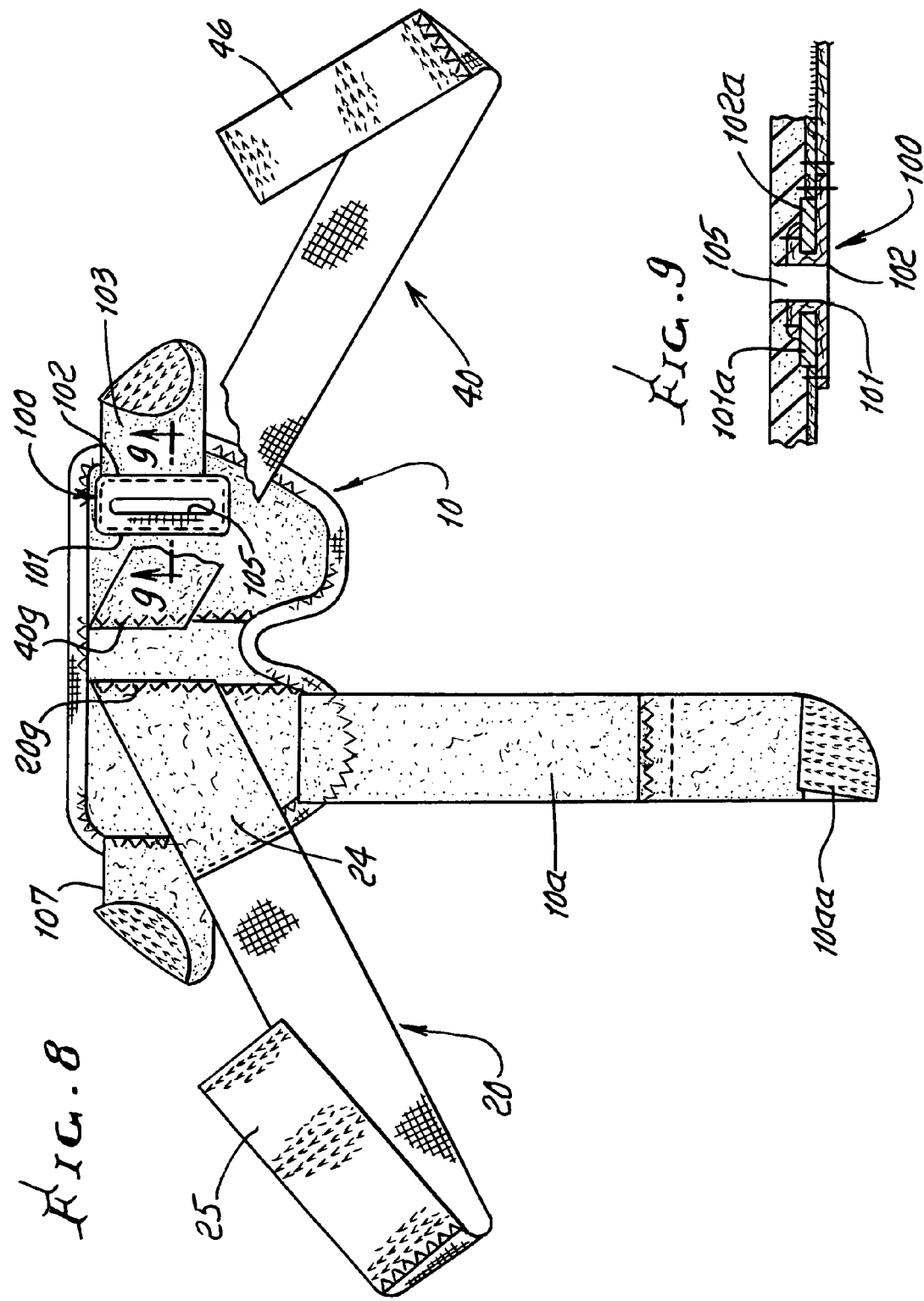

HIGHLY STABLE ANKLE BRACE

BACKGROUND OF THE INVENTION

This invention relates generally to ankle braces, and more particularly to improvements in such braces enabling ease and rapidity of application to the wearer's ankle, a well as enhanced ankle stability.

Injuries to ankles such as sprains frequently require the application of ankle braces, which must be repeatedly applied and removed at frequent intervals. Accordingly, ease and rapidity of application and removal are essential. There is need for improvements in ankle braces enabling such ease and rapidity of brace application and removal, as well as providing for enhanced ankle stability and support when applied.

SUMMARY OF THE INVENTION

It is a major object of the invention to provide an improved ankle brace meeting the above needs. Basically, the ankle brace apparatus embodying the invention preferably comprises:

a) a foot and ankle holder having a lower foot portion, and having an upper ankle portion with opposite first and second sides, said upper ankle portion including:
  i) a guide loop having opposite sections,
  ii) a first orthopedic strap anchored to one section for passing about a user's ankle or lower leg, and then passage through the loop to extend in a first tightening direction,
  iii) a second orthopedic strap anchored to another said section to extend in a second and opposite tightening direction, relative to said ankle or lower leg,
  iv) whereby the two straps extending in said first and second directions can be manually pulled in said directions to tighten the first strap about said ankle or lower leg,
  v) and the two tensioned straps then connected by push together connection to tightened extents of the first strap to hold tension transmission via said loop sections and straps, b) support strap structure operatively connected to said holder to extend under said foot portion and then to extend generally upwardly and rearwardly for removable retention to at least one of said opposite sides at a retention zone, or zones.

A further object is to provide such support strap structure which includes two support straps wrapped in opposite directions under said holder foot portion, said support straps having first end portions which have hinge attachments to said holder upper ankle portion opposite first and second sides, respectively. Such hinge attachments are preferably spaced apart to provide freely exposed strap free cushioning at the rear of said holder. Also, the holder foot portion has hook and pile connection to said two support straps.

Another object is to configure the rear of the holder to be free of any overlying strap structure between the uppermost and lowermost extents thereof, whereby said cushioning is unrestricted by any strap structure, and said rear of the holder provides a strap free conforming cushion. As will be seen, the holder foot portion has hook and pile connection to said support strap structure.

Yet another object is to provide the support strap structure to include two support straps wrapped in opposite directions under said holder foot portion.

An added object is to provide the push together connections at four spaced locations on said straps. Two of such spaced locations are typically associated with the first direction, and a second two of said spaced locations are associated with said second direction.

A further object is to provide the loop with stretches that are tensioned during said tension transmission via the loop sections. Also, the loop is sufficiently stiff to withstand opposite directional tensioning of the tightener straps, without substantial loop endwise deflection, while maintaining the first and second straps oriented in general alignment proximate the loop to prevent tensioning misalignment. As will be seen, the loop defines a bounded area such as a slit free of any retention structure other than the strap passing therethrough.

Additionally, the first and second straps have positions characterized in that endwise tensioning of strap end portions is established and maintained while forcible face to face operative connection of strap extents is simultaneously established at two endwise spaced locations.

Yet another object is to provide improved brace apparatus comprising:

a) a flexible holder structure fittingly attachable to the user's foot and ankle, b) said holder structure include anchoring strap structure having means to endwise tension the anchoring strap structure about the user's limb proximate the ankles, c) and support straps having certain ends attached to the anchored holder structure to be wrapped directionally oppositely about the ankle and foot of the user and then upwardly to terminate opposite sides of the holder structure, d) thereby to provide at least three layers of overlapping strap material at each side of the holder structure with hook and pile material providing positive anchoring interconnection of said layers.

These and other objects and advantages of the invention, as well as the details of an illustrative embodiment, will be more fully understood from the following specification and drawings, in which:

DRAWING DESCRIPTION

FIG. 8 is a plan view showing the holder with its straps, extending in a substantially flat or extended plane;

FIG. 9 is an enlarged view taken on lines 9-9 of FIG. 8,

DETAILED DESCRIPTION

Figure 1:
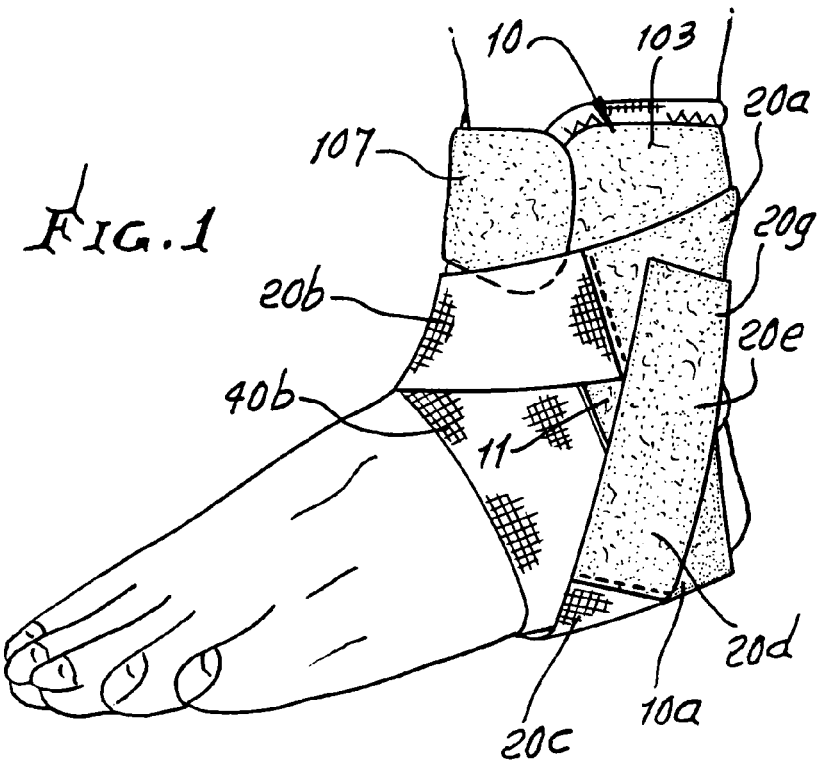
FIG. 1 is a frontal and left side elevation in perspective, showing apparatus embodying one preferred form of the invention, as applied to a wearer's left foot and ankle, with all straps in position.

In the preferred embodiment shown, a holder in the form of a boot 10 for the foot and ankle of a wearer is shown to have a lower foot portion 10a and an upper ankle portion 10b.

Opposite panel sides of the portion 10b are indicated at 11 and 12. Side 11 is at the outer side of the ankle, and side 12 is at the inner side of the ankle. The rear side of the holder is seen at 13, and a lower cut-out 13a is formed in 13 to receive the heel of the wearer. The holder may consist of non-stretchable Nylon fabric, which is durable and flexible.

Figure 5:
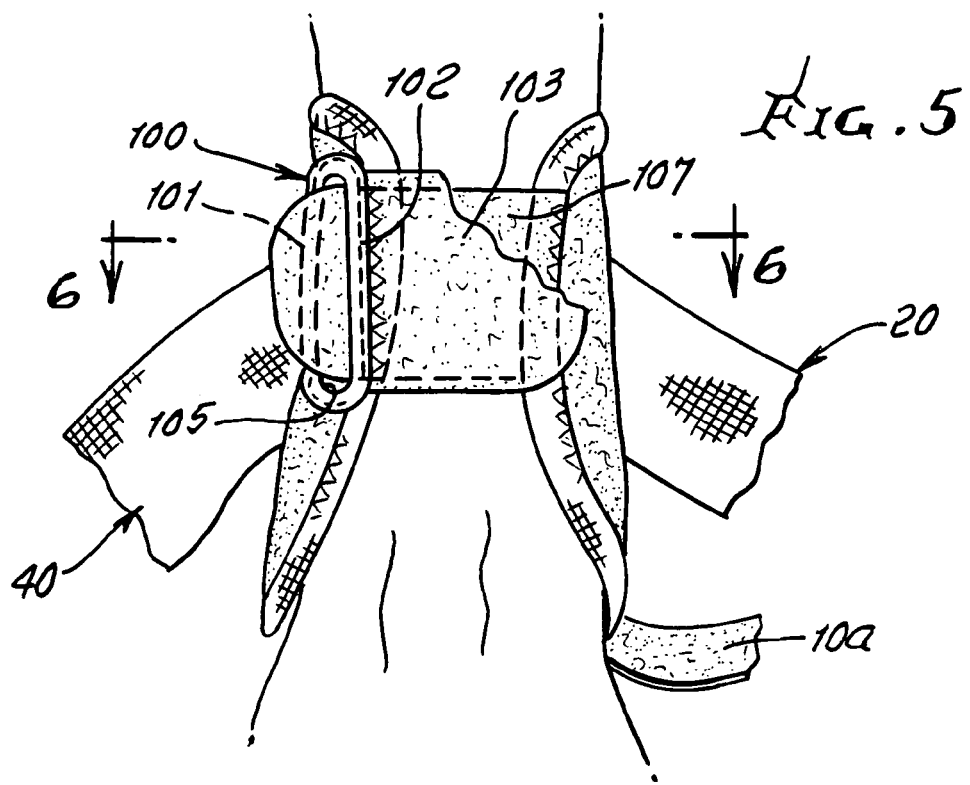
FIG. 5 is a frontal view, showing straps in uncompletely attached relation.
Figure 6:
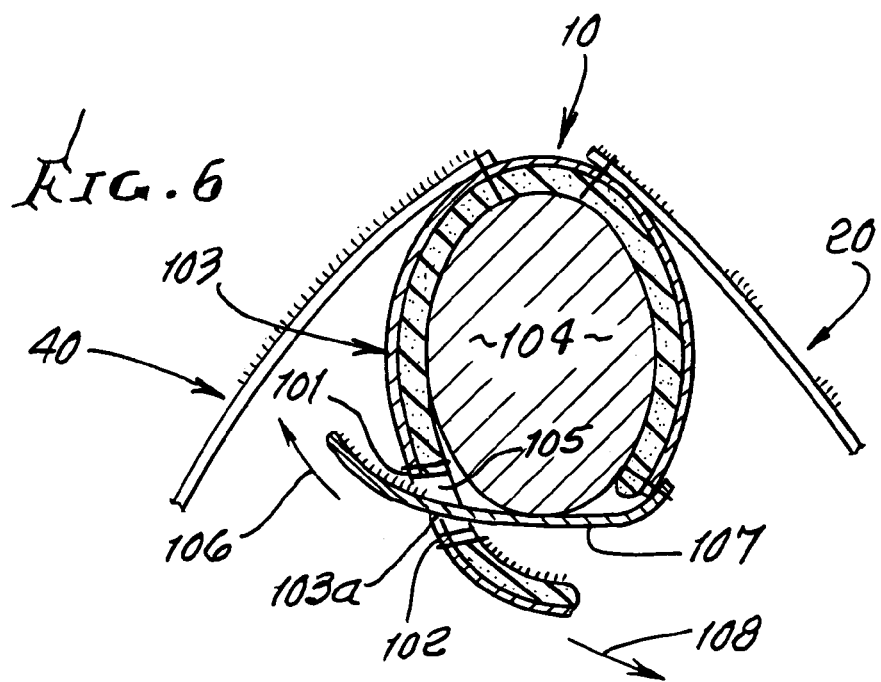
FIG. 6 is a section taken on likes 6-6 of FIG. 5, showing an initial step in strap attachment.
Figure 7:
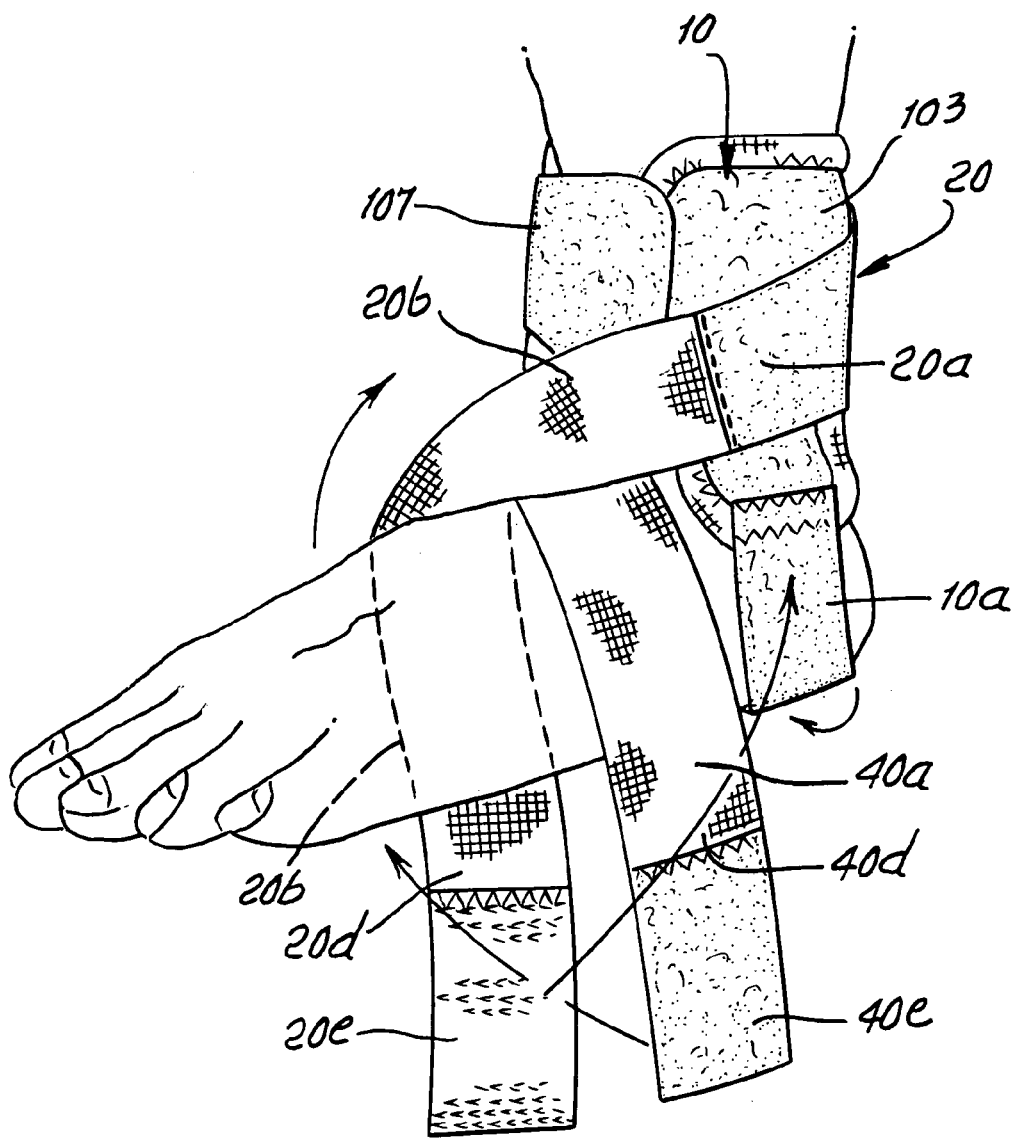
FIG. 7 is a view like FIG. 1, showing a subsequent step in strap attachment.

Extending the description to FIGS. 5, 6, and 8, the holder upper ankle portion typically includes:

i) a guide loop 100 having opposite sections 101 and 102,
ii) a first flexible orthopedic strap 103 anchored to one section, such as section 101, for passing about a user's ankle 104 or lower leg, and then passage at 103a through the loop at slit 105 to extend in a first tightening direction 106,
iii) a second flexible orthopedic strap 107 anchored to another said section, such as section 102, to extend in a second and opposite tightening direction, 108, relative to said ankle or lower leg,
iv) whereby the two straps 103 and 107 extending in said first and second directions can be manually pulled in said directions to tighten the first strap 103 about said ankle or lower leg,
v) and the two tensioned straps can then be connected by push together connection (for example by hook and pile) to tightened or tensioned extents of the first and second straps to hold tension transmission via said loop, sections and straps. The holder is thereby positively connected to the ankle or leg.

Figure 3:
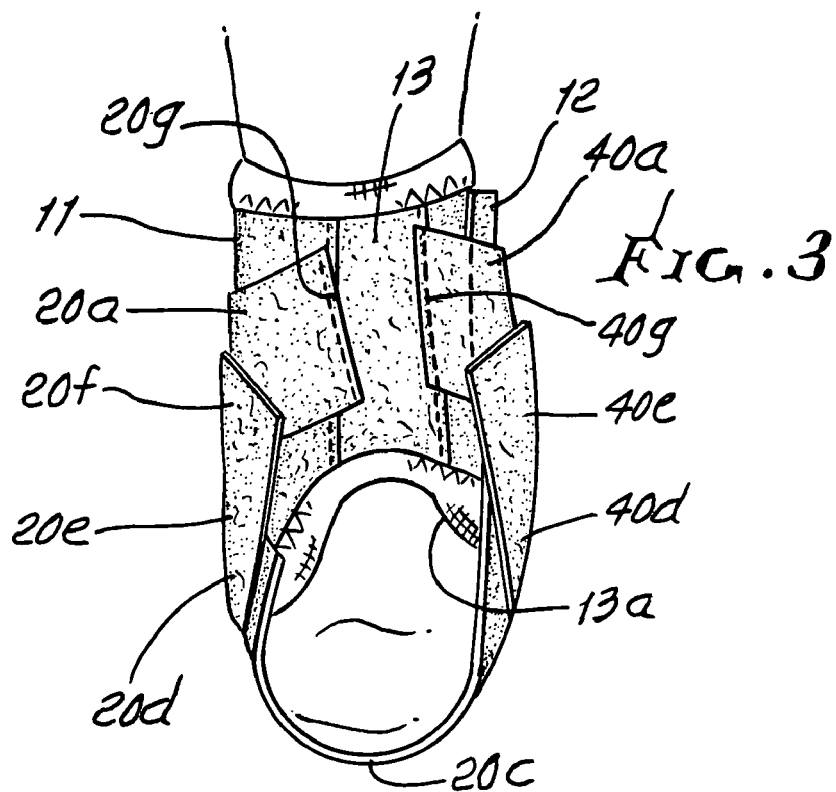
FIG. 3 is a rear elevation of the FIG. 1 apparatus showing its application to the heel.
Figure 4:
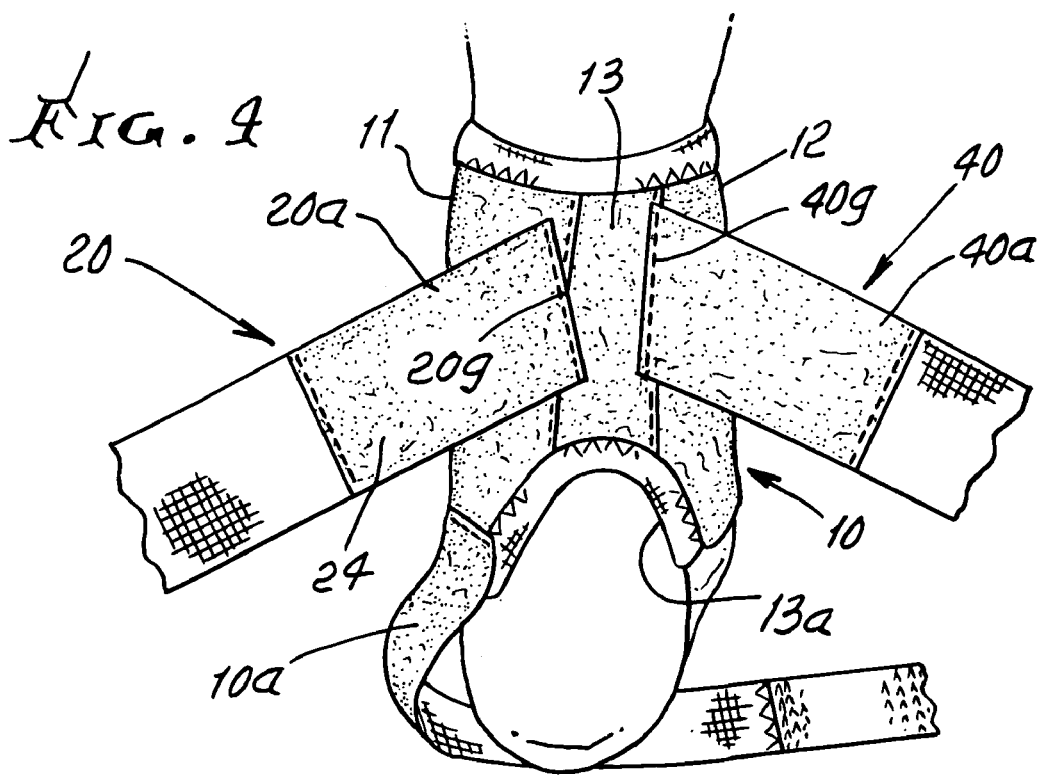
FIG. 4 is a rear view like FIG. 3 but showing straps in unattached relation.

Flexible support strap structure is provided, and is operatively connected to the holder 10 to extend under foot portion 10a and then to extend generally upwardly for retention to opposite holder sides 11 and 12, at retention zones. See for example FIGS. 3 and 4 showing strap 20 having one end portion 20a hinge connected at 20g as by stitching to the holder side 11, above ankle level, the strap 20 then extending forwardly and downwardly at 20b across the upper straps 103 and 107, then downwardly under the lower foot portion 10a of the holder at 20c, then back upwardly at 20d at the side of the ankle for operative connection as by hook and pile connection of strap opposite end portion 20e to the holder side 11, typically in overlying connected (hook and pile) relation to end portion 20a at 20f. The operative connection may advantageously consist of inner side hook and pile material 25 connected to outer pile or hook material 24 on 20a. Similarly, a second support strap 40 is provided to have one end portion 40a hinge connected at 40g to the holder side 12, above ankle level, the strap then extending forwardly and downwardly at 40b across the upper straps 103 and 107, under strap extent 20b and then downwardly and under the lower foot portion of the holder at 40c, crossing 20c, and then back upwardly at 40d at the opposite side of the ankle, for operative connection of strap 40 opposite end portion 40e to the holder, typically in overlying relation to end portion 40a. Such operative connection may advantageously consist of inner side hook or pile material at 46 connected to outer pile or hook material 49 on 40a. Lowermost holder structure under the foot also carries hook or pile material to connect to pile or hook material on straps at 20c or 40c.

Figure 2:
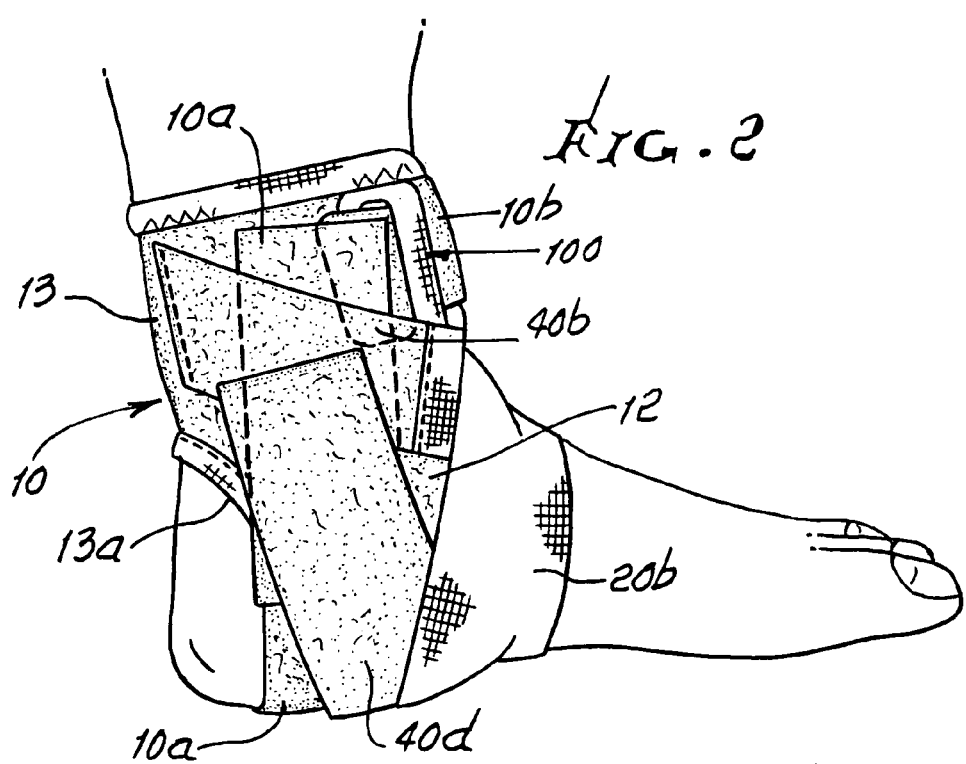
FIG. 2 is a right side and rear elevation, in perspective, of the FIG. 1 apparatus.

FIG. 9 shows the guide loop 100 having metallic stiffeners 101a and 102a within sections 101 and 102, respectively. FIG. 2 also shows foot portion 10a wrapping upwardly at a side of the holder portion 10b to attach thereto at 10aa.

In summary, multiple support straps as at 20 and 40 are provided to overlie one another, such as a pair or more of overlying strap extents 40b and 40e, and/or a pair or more of overlying strap extents 20b and 20e, to increase the strength and/or stiffness of the ankle brace composite, at the side or sides of the ankle, such overlying strap extents reinforcing anchored to the first and second straps 103 and 107 which are themselves positively tension connected to the leg or arm, as described above. Strap 103 also provides a cushion between uppermost and lowermost extents of the rear of the holder, to comfortably adjust to the wearer's foot at the thereby unconstrained Achilles tendon area, and at the same time, the ankle brace performs its positive ankle bracing functions. Note that no straps overlie the Achilles tendon area at the rear of the holder.

Figure 10:
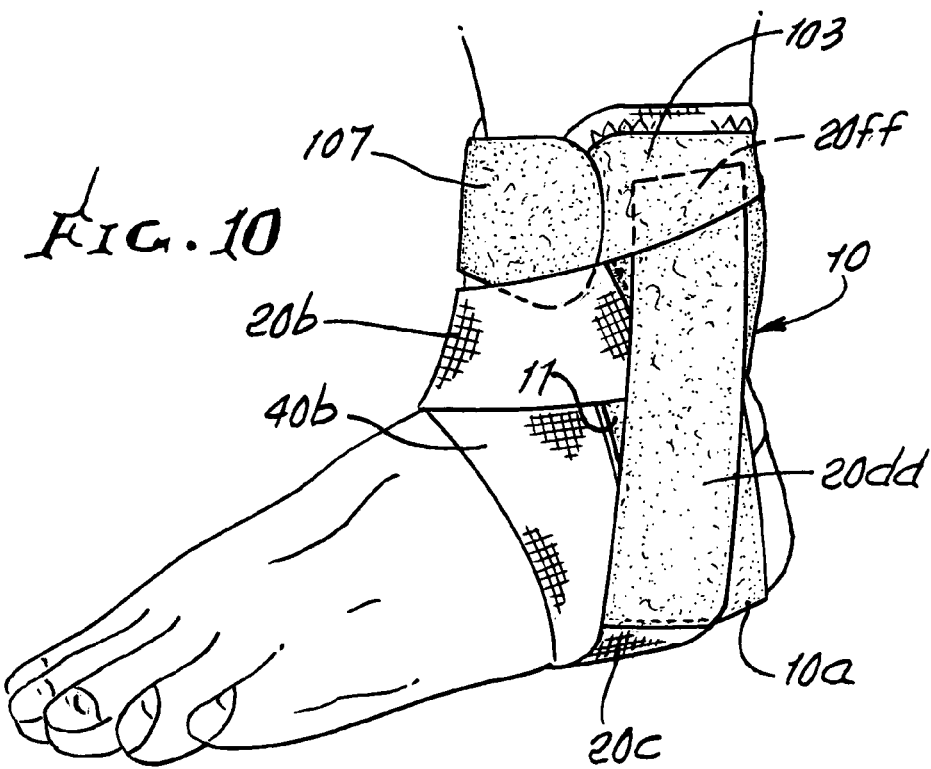
FIG. 10 is a view like FIG. 1 showing a modification.
Figure 11:
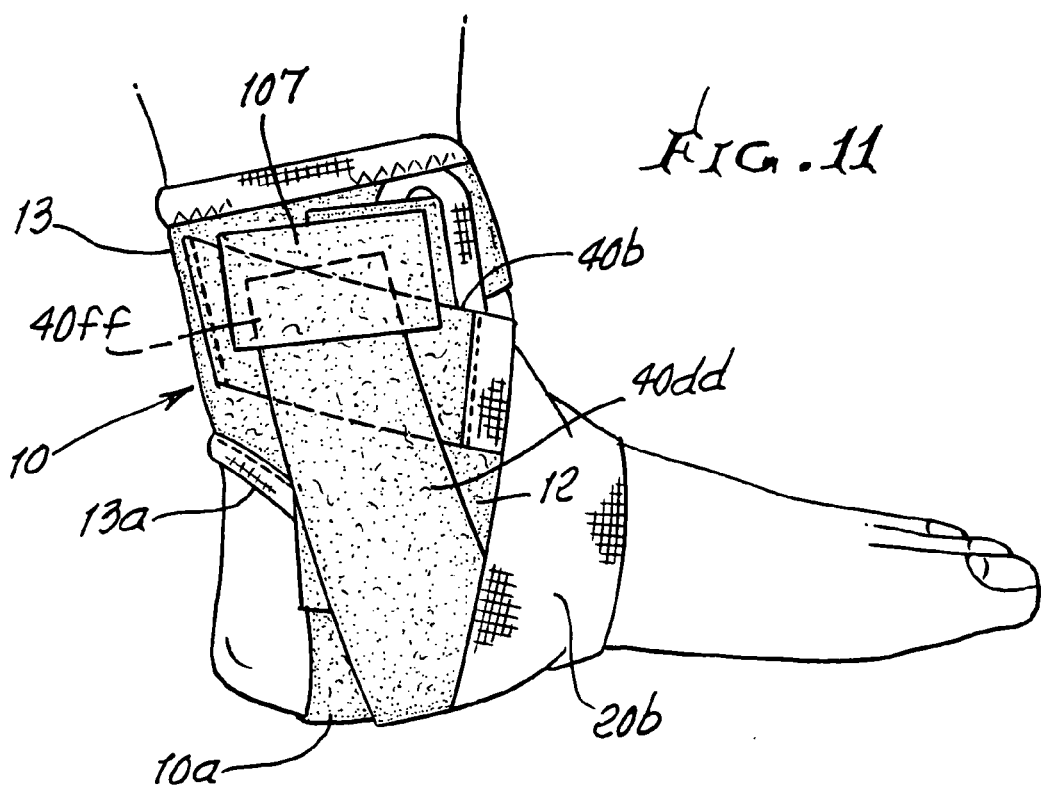
FIG. 11 is a view like FIG. 2 showing an additional modification.

In the FIGS. 10 and 11 modifications, the support strap 20dd, corresponding to strap 20d in FIG. 1, extends upwardly at 20ff beneath strap 103, such as an end portion thereof and is removably connected to 103 by hook and pile connection material, whereby the straps 103 and 107 assist in holding 20ff and 20dd in generally extended and firmly attached position. The illustrated FIG. 10 elements are otherwise like those in FIG. 1.

Also in the FIGS. 10 and 11 modification, the support strap 40dd, corresponding to strap 40d in FIG. 2, extends upwardly at 40ff beneath strap 107, such as beneath an end flap portion thereof and is removably connected to 107 by hook and pile connection material, whereby the straps 103 and 107, which are endwise interconnected, assist in holding 40dd and 40ff in upwardly extended and firmly attached position. Note that strap extent 40ff overlaps strap extent 40b, and that strap 107 overlaps both 40ff and 40b, to provide a three interconnected layer assembly. The illustrated FIG. 11 elements are otherwise like those in FIG. 2.

I claim:

1. In ankle brace apparatus, the combination comprising
a) a foot and ankle holder having a lower foot portion, and having an upper ankle portion with opposite first and second sides, said upper ankle portion including:
i) a guide loop having opposite sections,
ii) a first orthopedic strap anchored to one section for passing about a user's ankle or lower leg, and then passage through the loop to extend in a first tightening direction,
iii) a second orthopedic strap anchored to another said section to extend in a second and opposite tightening direction, relative to said ankle or lower leg,
iv) whereby the two straps extending in said first and second directions can be manually pulled in said directions to tighten the first strap about said ankle or lower leg,
v) and the two tensioned straps then connected by push together connection to tightened extents of the first strap to hold tension transmission via said loop sections and straps,
b) support strap structure operatively connected to said holder to extend under said foot portion and then to extend generally upwardly and rearwardly for removable retention to at least one of said opposite sides at a retention zone, or zones,
c) wherein in planar flattened and extended position of the brace the first strap extends leftwardly and angularly downwardly, said second strap extends rightwardly and angularly downwardly, and said support strap structure is elongated and extends downwardly between said first and second straps and forms acute angles therewith, said first and second straps having anchoring ends located at substantially the same zone of the holder structure.

2. The combination of claim 1 wherein said support strap structure includes two support straps wrapped in opposite directions under said holder foot portion, said support straps having first end portions which have hinge attachments to said holder upper ankle portion opposite first and second sides, respectively.

3. The combination of claim 2 wherein said hinge attachments are spaced apart to provide freely exposed strap free cushioning at the rear of said holder.

4. The combination of claim 3 wherein said rear of the holder is free of any overlying strap structure between the uppermost and lowermost extents thereof, whereby said cushioning is unrestricted by any strap structure, and said rear of the holder provides a strap free conforming cushion.

5. The combination of claim 2 wherein said holder foot portion has hook and pile connection to said two support straps.

6. The combination of claim 2 wherein said support straps have second end portions captivated by at least one of said orthopedic straps.

7. The combination of claim 2 wherein at least one of said support straps has a second upwardly extending end portion captivated by at least one of said orthopedic straps.

8. The combination of claim 1 wherein said holder foot portion has hook and pile connection to said support strap structure.

9. The combination of claim 8 wherein said support strap structure includes two support straps wrapped in opposite directions under said holder foot portion.

10. The combination of claim 1 wherein said push together connections are at four spaced locations on said straps.

11. The combination of claim 10 wherein two of said spaced locations are associated with said first direction, and a second two of said spaced locations are associated with said second direction.

12. The combination of claim 11 wherein hook and pile material is on said tightened extent of the first strap.

13. The combination of claim 11 wherein hook and/or pile material is located at said first two locations, and hook and/or pile material is also located at the second of said locations.

14. The combination of claim 1 where the loop has stretches that are tensioned during said tension transmission via the loop sections.

15. The combination of claim 1 wherein the first and second straps have terminals spaced from said loop to enable manual grasping and pulling of the two straps in said directions for tightening and loosening of the first and second straps about the user's ankle or lower leg.

16. The combination of claim 1 wherein the guide loop is sufficiently stiff to withstand opposite directional tensioning of the tightener straps, without substantial loop endwise deflection, while maintaining the first and second straps oriented in general alignment proximate the loop to prevent tensioning misalignment.

17. The combination of claim 16 wherein the loop defines a bounded area free of any retention structure other than the strap passing therethrough.

18. The combination of claim 1 wherein the first and second straps have positions characterized in that endwise tensioning of strap end portions is established and maintained while forcible face to face operative connection of strap extents is simultaneously established at two endwise spaced locations.

* * * * *